US012582467B2

(12) United States Patent
Dickerson

(10) Patent No.: US 12,582,467 B2
(45) Date of Patent: Mar. 24, 2026

(54) SURGICAL INSTRUMENT WITH HOVER SENSOR AND RELATED METHODS

(71) Applicant: Cilag GmbH International, Zug (CH)

(72) Inventor: Benjamin D. Dickerson, San Francisco, CA (US)

(73) Assignee: Cilag GmbH International, Zug (CH)

( * ) Notice: Subject to any disclaimer, the term of this patent is extended or adjusted under 35 U.S.C. 154(b) by 467 days.

(21) Appl. No.: 18/093,165

(22) Filed: Jan. 4, 2023

(65) Prior Publication Data

US 2024/0216044 A1 Jul. 4, 2024

(51) Int. Cl.
*A61B 18/14* (2006.01)
*A61B 17/00* (2006.01)
*A61B 18/00* (2006.01)

(52) U.S. Cl.
CPC ...................... *A61B 18/1492* (2013.01); *A61B 2017/00199* (2013.01); *A61B 2018/00577* (2013.01); *A61B 2018/00696* (2013.01); *A61B 2018/00702* (2013.01); *A61B 2018/00732* (2013.01); *A61B 2018/00761* (2013.01); *A61B 2018/00875* (2013.01); *A61B 2018/00904* (2013.01)

(58) Field of Classification Search
CPC ...... A61B 18/1492; A61B 2017/00199; A61B 2017/00026; A61B 2018/00577; A61B 2018/00696; A61B 2018/00702; A61B 2018/00732; A61B 2018/00761; A61B 2018/00875; A61B 2018/00904; A61B 34/00
USPC .......................................................... 606/41
See application file for complete search history.

(56) References Cited

U.S. PATENT DOCUMENTS

| | | | |
|---|---|---|---|
| 9,763,741 B2 | 9/2017 | Alvarez et al. | |
| 10,166,082 B1 | 1/2019 | Hariri et al. | |
| 10,464,209 B2 | 11/2019 | Ho et al. | |
| RE47,996 E * | 5/2020 | Turner ..................... | A61N 7/00 |
| 10,667,875 B2 | 6/2020 | DeFonzo et al. | |

(Continued)

FOREIGN PATENT DOCUMENTS

WO      WO-2021062373 A2 *    4/2021    ............. A61B 34/76

OTHER PUBLICATIONS

International Search Report and Written Opinion dated Apr. 29, 2024, for International Application No. PCT/IB2024/050020, 14 pages.

*Primary Examiner* — Beverly M Flanagan
(74) *Attorney, Agent, or Firm* — FBT Gibbons LLP

(57) ABSTRACT

A robotic surgical system, including: a robotic arm including a distal end; a tool driver operatively coupled with the distal end of the robotic arm; a control unit; a surgical instrument including: an end effector configured to transmit therapeutic energy to tissue via a therapeutic energy cycle based on instructions from the control unit; and an tissue sensor configured to determine at least one tissue characteristic and transmit the at least one tissue characteristic to the control unit, wherein the control unit is configured to modify the therapeutic energy cycle based on the at least one tissue characteristic; and a control console including: an activation switch configured to activate the therapeutic energy cycle, and a hover sensor configured to sense an object within a hover zone, wherein the hover sensor is configured to activate the tissue sensor to determine the at least one tissue characteristic.

20 Claims, 10 Drawing Sheets

(56)        References Cited

U.S. PATENT DOCUMENTS

| | | |
|---|---|---|
| 10,765,303 B2 | 9/2020 | Graetzel et al. |
| 10,827,913 B2 | 11/2020 | Ummalaneni et al. |
| 10,881,280 B2 | 1/2021 | Baez, Jr. |
| 10,888,383 B2 | 1/2021 | Cone et al. |
| 10,898,277 B2 | 1/2021 | Srinivasan et al. |
| 11,058,493 B2 | 7/2021 | Rafii-Tari et al. |
| 11,071,595 B2 | 7/2021 | Johnson et al. |
| 11,278,361 B2 | 3/2022 | Gonenc et al. |
| 2009/0254080 A1* | 10/2009 | Honda ............... A61B 18/1402 606/38 |
| 2019/0231382 A1* | 8/2019 | Inoue ................. A61B 18/1442 |
| 2022/0401143 A1 | 12/2022 | Sims |
| 2024/0090962 A1 | 3/2024 | Itkowitz et al. |

* cited by examiner

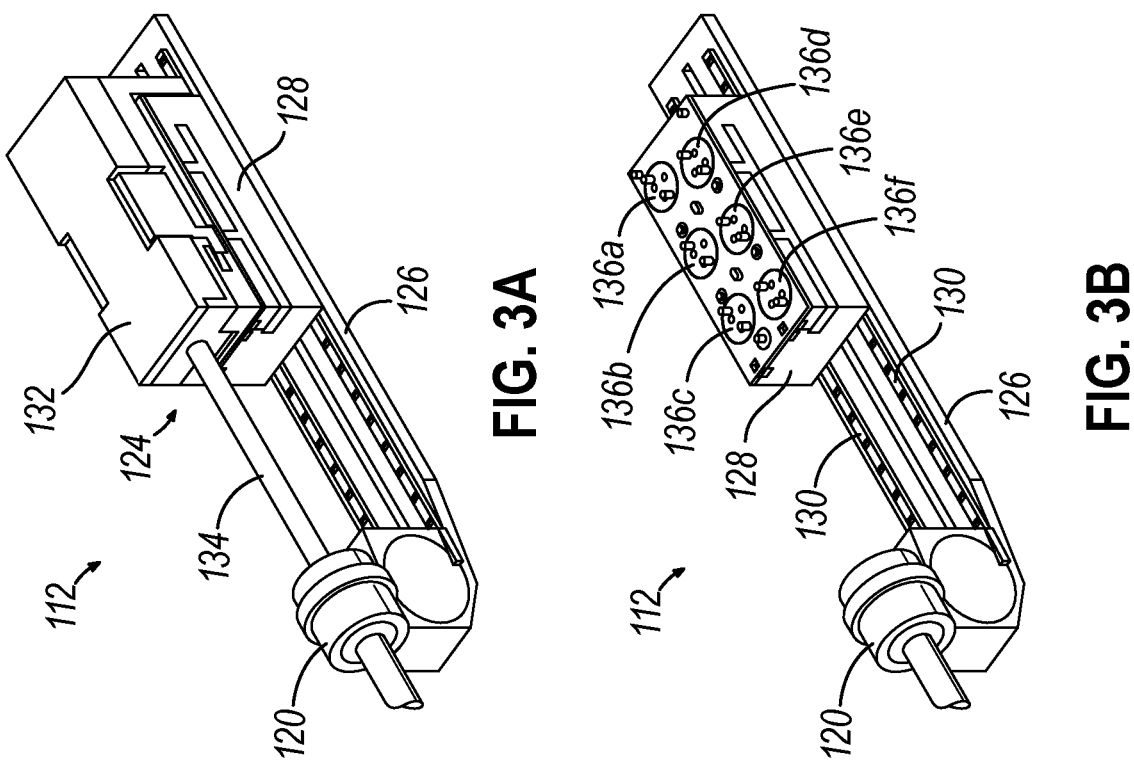
FIG. 3A
FIG. 3B
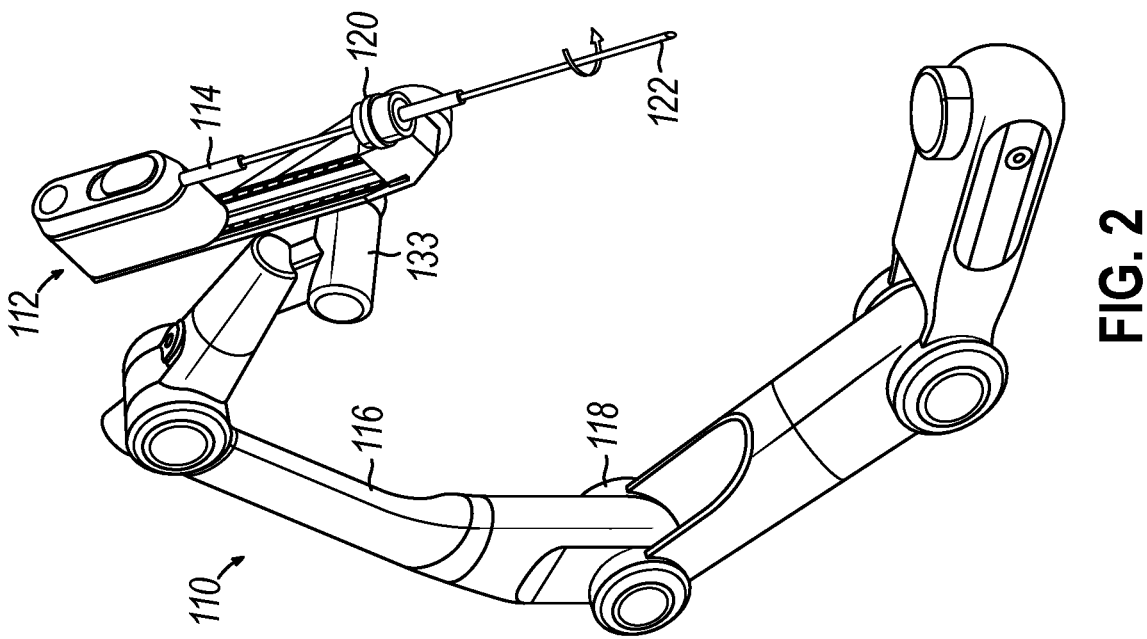
FIG. 2

SURGICAL INSTRUMENT WITH HOVER SENSOR AND RELATED METHODS

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more input devices (such as foot pedals, joysticks, exoskeletol gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 2 depicts a perspective view of an example of a robotic arm, an example of a tool drive, and an example of a surgical instrument, each configured with use with the table-based robotic system of FIG. 1;

FIG. 3A depicts an enlarged schematic perspective view of the tool driver and surgical instrument of FIG. 2;

FIG. 3B depicts an schematic perspective view of the tool driver similar to FIG. 3A, but with the surgical instrument removed to expose rotary drives;

DETAILED DESCRIPTION

I. Overview of Example of Robotic Surgical System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the clinician. Additionally, the system may provide the clinician with the ability to perform the procedure from an ergonomic position without the need for awkward arm motions and positions. Still further, the system may provide the clinician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Table

Figure 1:
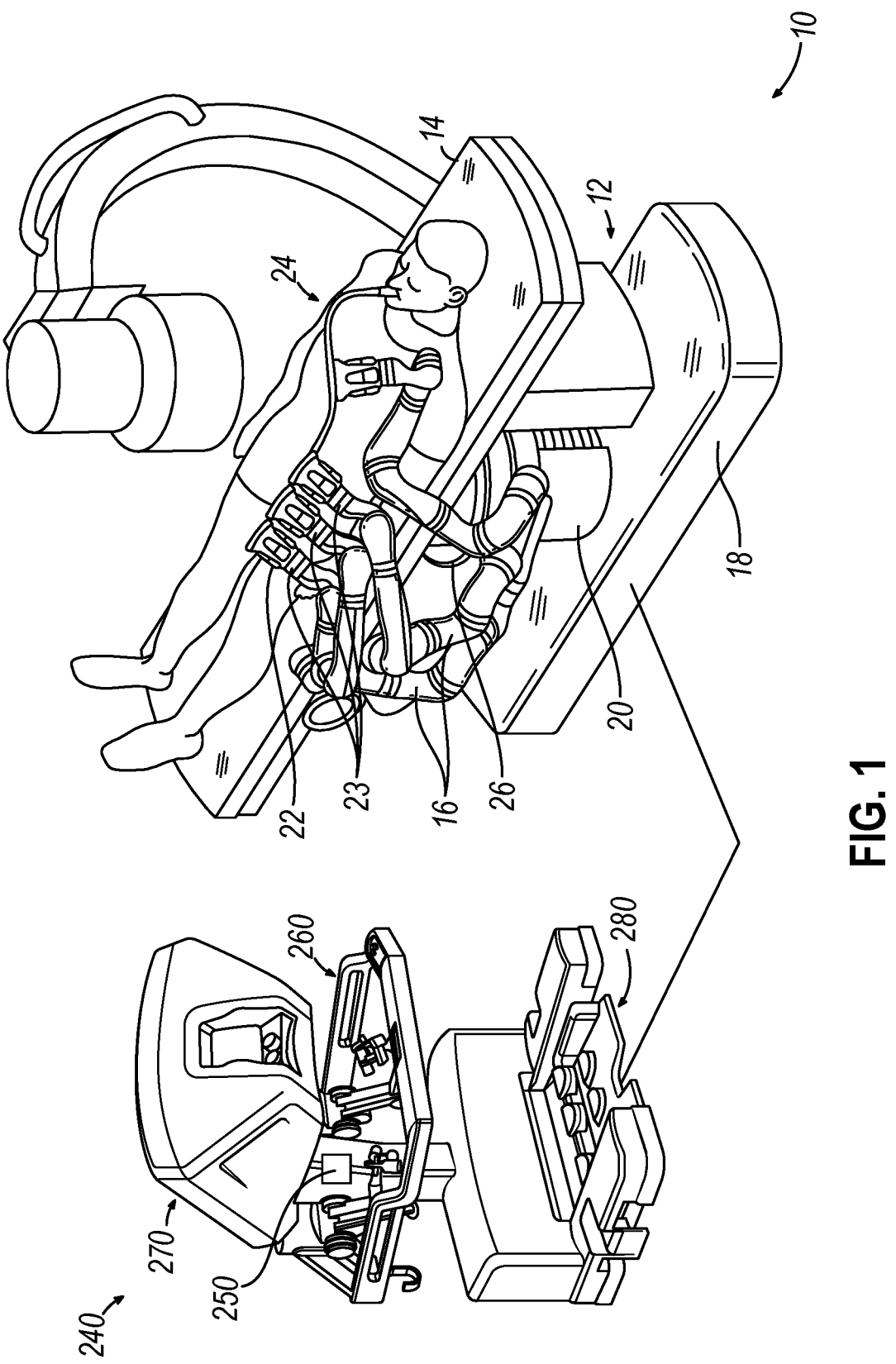
FIG. 1 depicts a perspective view of an example of a table-based robotic system that includes a surgeon console and a plurality of robotic arms.

FIG. 1 illustrates an example of a robotic surgical system (10). Robotic surgical system (10) includes a support structure (12) for supporting a platform (14) (shown as a "table" or "bed") over the floor and one or more robotic arms (16). Support structure (12) includes a base (18) and a column (20). Column (20) structurally supports platform (14) and provides a path for vertical translation of the carriages. In some versions, a table base may stow and store robotic arms (16) when not in use. Column (20) of the present example also includes a ring-shaped carriage (26), from which robotic arms (16) are based. A surgeon console (240) is coupled with robotic surgical system (10).

Robotic arms (16) are shown as part of a table-mounted system, but in other configurations, robotic arms (16) may be mounted in a cart, ceiling or sidewall, or other suitable support surface. Robotic arms (16) are shown as extending from column (20) via carriage (26). However, robotic arms (16) may be coupled with robotic surgical system (10) using a variety of suitable structures. While robotic arms (16) are all shown as being positioned on one side of the patient in FIG. 1, other configurations may position robotic arms (16) on both sides of the patient, between the legs of the patient, and/or in any other suitable locations. Tool drivers (22) are positioned at distal ends of robotic arms (16) in the present example. Tool drivers (22) are operable to manipulate one or more surgical instruments (24), as will be described in greater detail below.

Surgeon console (240) includes a control unit (250), a hand-control console (260), a display unit (270), and a foot control console (280). As will be described in greater detail below, surgeon console (240) may be utilized by a surgeon in order to view suitable data (e.g. visual images of the surgical site, current status of various system (10) components, etc.) and/or to manipulate robotic arms (16), tool drivers (22), and/or surgical instruments (24) during a surgical procedure.

B. Example of a Robotic Arm, Tool Drive, and Tool

FIG. 2 shows an example of a robotic arm (110), a tool driver (112), and a surgical instrument (114), which may be incorporated into robotic surgical system (10) in place of robotic arm (16), tool driver (22), and surgical instrument (24) that are shown in FIG. 1. Additional examples of robotic arms, a tool drivers, and a surgical instruments are shown and described in U.S. Pat. No. 10,166,082, entitled "System and Method for Controlling a Robotic Wrist," issued Jan. 1, 2019, the disclosure of which is incorporated by reference herein, in its entirety.

As shown in FIG. 2, robotic arm (110) includes a plurality of links (116) and a plurality of joints (118) for actuating links (116) relative to one another. Tool driver (112) is attached to the distal end of robotic arm (110). Tool driver (112) includes a cannula (120) coupled to the end of tool driver (112), to receive and guide surgical instrument (114). Surgical instrument (114) may include an endoscope, a laparoscope, a stapler, graspers, an ultrasonic instrument, an RF electrosurgical instrument, or any other suitable kind of instrument. Surgical instrument (114) is inserted into the patient via cannula (120). The distal end of surgical instrument (114) includes an end effector (122). End effector (122) is configured to interact with the patient (e.g., providing visualization, stapling, grasping, ultrasonic cutting and/or sealing, electrosurgical cutting and/or sealing, etc.).

Joints (118) of robotic arm (110) may be actuated to selectively position and orient tool driver (112), which actuates the end effector (122) for robotic surgeries. Joints (118) may include various types, such as a pitch joint or a roll joint, which may substantially constrain the movement of the adjacent links (116) around certain axes relative to other links (116). Each joint (118) represents an independent degree of freedom available to robotic arm (110). A multitude of joints (118) result in a multitude of degrees of freedom, allowing for "redundant" degrees of freedom. Redundant degrees of freedom allow the robotic arms (110) to position their respective end effectors (122) at a specific position, orientation, and trajectory in space using different positions links (116) and angles of joints (118). This allows for the system to position and direct a surgical instrument (114) from a desired point in space while allowing the clinician to move joints (118) into a clinically advantageous position away from the patient to create greater access, while avoiding collisions of robotic arms (110).

FIGS. 3A and 3B show tool driver (112) with and without a tool driver adapter (124), which may also be referred to as a tool base. As shown in FIGS. 3A and 3B, tool driver (112) may include a stage (126) and a carriage (128). Stage (126) includes longitudinal tracks (130). Carriage (128) is slidingly engaged with longitudinal tracks (130). Stage (126) may be configured to couple to the distal end of robotic arm (110) such that articulation of robotic arm (110) positions and/or orients tool driver (112) in space. Surgical instrument (114) includes a tool driver adapter (124) at a proximal end and, as noted above, end effector (122) at a distal end. Tool driver adapter (124) includes a handle (132) and a shaft assembly (134) that extends distally from handle (132).

Carriage (128) is configured to couple with tool driver adapter (124). Carriage (128) may drive a set of articulated movements of end effector (122) and/or otherwise actuate end effector (122), such as through a cable system or wires manipulated and controlled by actuated drives. Carriage (128) may include different configurations of actuated drives, including but not limited to motorized rotary axis drives. The plurality of rotary axis drives may be arranged in any suitable manner. As shown in FIG. 3B, carriage (128) of the present example includes six rotary drives (136a-f) arranged in two rows, extending longitudinally along the base of carriage (128). Rotary drives (136a-c) are arranged in a first row that is longitudinally offset from a second row in which rotary drives (136d-f) are arranged. This staggered arrangement of rotary drives (136a-f) may reduce the width of carriage (128) and thereby provide a more compact form factor for tool driver (112). However, rotary drives (136a-f) may be provided in any other suitable arrangement. Moreover, any other suitable kind(s) of drive outputs may be provided by carriage (128), in addition to or in lieu of rotary drives (136a-f).

II. Example of a Surgical Instrument with Hover Sensor

A. Overview of Surgeon Console

Figure 4:
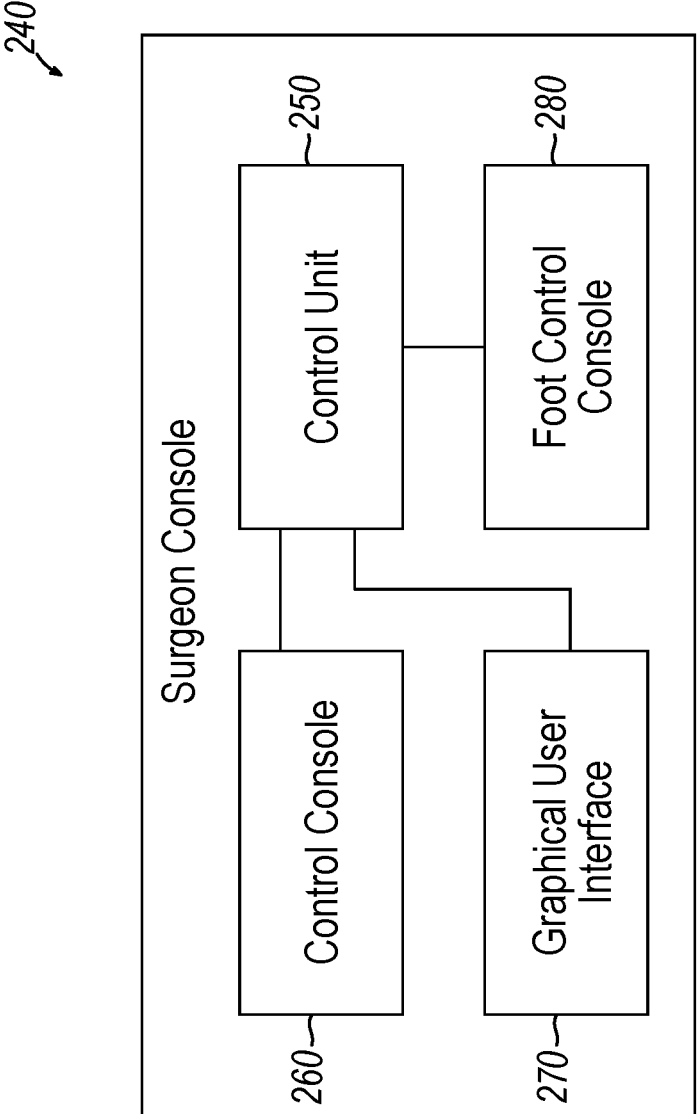
FIG. 4 depicts a schematic view of the surgeon console of FIG. 1 that includes a control unit, a control console, a display unit, and a foot control console.

FIG. 4 shows surgeon console (240) of FIG. 1. As mentioned above, surgeon console (240) may be utilized by a surgeon in order to view suitable data (e.g. visual images of the surgical site, current status of various system (10) components, etc.) and/or to manipulate robotic arms (16), tool drivers (22), and/or surgical instruments (24) during a surgical procedure. Surgeon console (240) includes control unit (250), control console (260), display unit (270), and foot control console (280).

Control unit (250) may include a processor, memory, a storage device, and/or any other suitable components capable of receiving, storing, processing, and transmitting data to/from suitable components of robotic surgical system (10). As shown in FIG. 4, control unit (250) is in communication with control console (260), display unit (270), and foot control console (280). Control unit (250) is also in communication with tool driver (112) such that control unit (250) may receive information originating from control console (260, 280) and suitably transmit such data to tool drivers (112) to thereby manipulate and control a respective surgical instrument (114) in accordance with the description herein. While control unit (250) in the current example is associated with surgeon console (240), this is merely optional. Control unit (250) may be associated with any other suitable component, or combination of combination of components as would be apparent to one skilled in the art in view of the teachings herein.

Control unit (250) may also be in communication with other suitable components of surgical instruments (114) or other suitable components of robotic surgical system (10). For example, control unit (250) may be in communication with various sensors of surgical instrument (114), such that control unit (250) may activate sensors, and/or acquire suitable data from sensors during exemplary use in accordance with the description herein. Control unit (250) may also receive and/or process data from suitable components of surgical system (10), and transmit such data to display unit (270), which may then visually display data for a surgeon to view.

Control console (260) may be in communication with control unit (250) and may be in the form of an input device or combination of input devices capable of receiving instructions from the operator and transmitting those instructions to control unit (250). Control console (260) may act as an interface between control unit (250) and operator such that operator may manipulate control console (260) to thereby transmit suitable data associated with such manipulation to control unit (250). Control console (260) may be utilized to assist control unit (250) in controlling tool drivers (112) to suitably utilize a respective surgical instrument (114) in accordance with the description herein. For example, control console (260) may be utilized to instruct tool driver (112) to move end effector (122) of surgical instrument (114) to suitably manipulate tissue in accordance with the description herein. Control console (260) may be in the form of a keyboard, control stick, camera, computer mouse or any other device capable of receiving instructions from an operator and transmitting instructions to control unit (250) as would be apparent to one skilled in the art in view of the teachings herein.

Display unit (270) may include a display or monitor capable of displaying suitable data to operator; such as video images of the surgical site, parameters of the robotic surgical system (10), etc. Display unit (270) may display information related to a patient and the status of suitable components of robotic arm (110) and surgical instrument (114). As discussed later, display unit (270) may indicate the status of end effector (310) (see FIG. 6) during exemplary use in accordance with the description herein.

Figure 5:
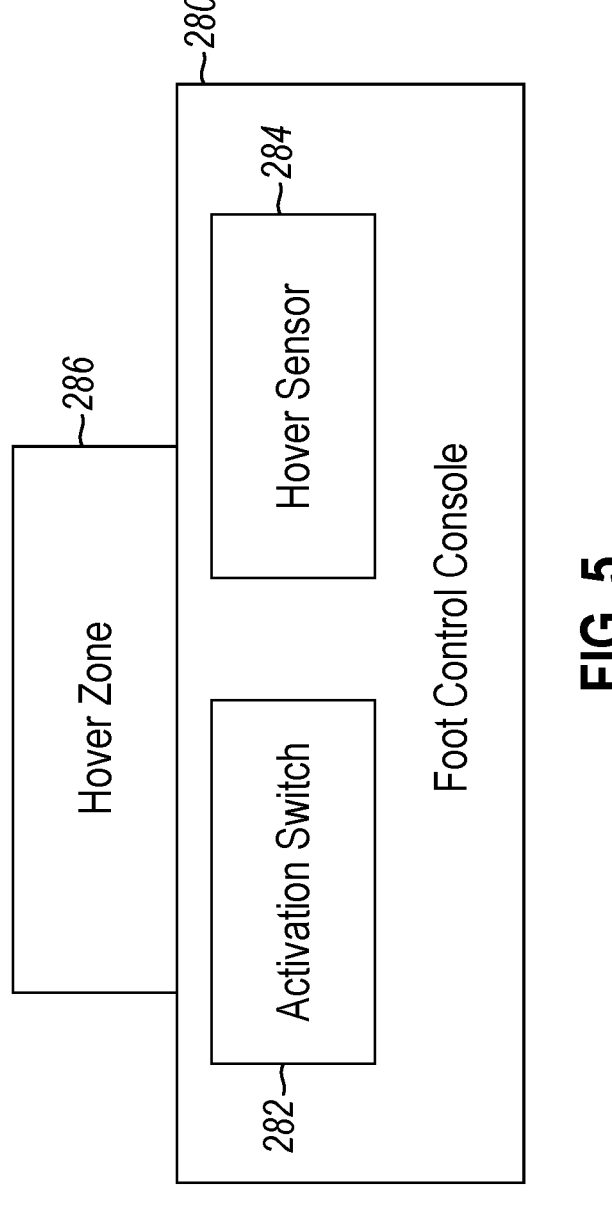
FIG. 5 depicts a schematic view of the foot control console of FIG. 4 that includes an activation switch and a hover sensor, the hover sensor having a hover zone.

B. Example of Foot Control Console Having Hover Sensor for Sub-Therapeutic Energy Delivery Turning to FIG. 5, foot control console (280) may be utilized to suitably manipulate and control surgical instruments (114). For example, foot control console (280) includes at least one activation switch (282). While one activation switch (282) is shown, two or more activation switches (282) may be utilized, as would be apparent to one skilled in the art in view of the teachings herein. Activation switch (282) may include a pedal that, when pressed by the operator, initiates a therapeutic energy delivery cycle.

For example, in instances where surgical instrument (114) includes end effector (122) configured to deliver RF energy; an operator may press pedal of activation switch (282) such that control unit (250) instructs surgical instrument (114) to deliver therapeutic energy onto tissue in the form of RF energy. As another example, in instances where surgical instrument (114) includes end effector (122) configured to deliver ultrasonic energy to tissue via an acoustic waveguide and ultrasonic blade; an operator may press pedal of activation switch (282) such that control unit (250) instructs surgical instrument (114) to deliver ultrasonic energy onto tissue. As yet another example, in instances where surgical instrument (114) includes an end effector (122) configured to grasp, sever, and staple tissue; an operator may press pedal of activation switch (282) such that control unit (250) initiates a firing cycle to sever and staple tissue.

In some instances, prior to delivering therapeutic energy to tissue, it may be desirable to obtain information regarding characteristics of such tissue. For example, it may be desirable to obtain information regarding the density of tissue, the type of tissue, or other suitable characteristics that would be apparent to one skilled in the art in view of the teachings herein. Further, it may be desirable to modify the therapeutic energy delivery cycle in response to the determined characteristics of such tissue, to thereby provide for customizable therapeutic results in response to the determined characteristics of tissue. For example, in instances where a specific type of tissue is detected, control unit (250) may modify a predetermined energy delivery cycle to increase/decrease the level of energy applied to tissue, as compared to if another type of tissue was detected. As another example, control unit (250) may modify the length and/or cyclical frequency at which energy is delivered to tissue. As yet another example, in instances where a pair of jaws grasp tissue, control unit (250) may instruct tool driver (112) to modify the grasping force applied to tissue prior to initiating the therapeutic energy delivery cycle.

However, accumulating tissue characteristic data and subsequently modifying the energy delivery cycle after pressing activation switch (282) may undesirably increase the amount of time for each therapeutic energy delivery cycle. Therefore, it may be desirable to accumulate such tissue characteristic data and substantially modify the energy delivery cycle prior to, yet in anticipation of, a surgeon physically pressing activation switch (282).

As mentioned above, foot control console (280) is in communication with control unit (250). Foot control console (280) includes activation switch (282) and a hover sensor (284). Activation switch (282) may be manipulated by an operator, such as the foot of an operator. Foot control console (280) may be positioned such that operator can use foot control console (280) with control console (260) simultaneously. In some examples, activation switch (282) includes an active and inactive position, such as with a maintained or momentary switch. While in the active position, activation switch (282) is operable to signal control unit (250) to activate a therapeutic energy delivery cycle of an end effector (such as end effector (310) shown in FIGS. 6-7C). Therefore, during exemplary use, a surgeon may utilize control console (260, 280) to manipulate an end effector operatively attached to robot arm (110) to suitably engage tissue at a surgical site. Once tissue at the surgical site is suitably engaged by the end effector, surgeon may press activation switch (282) to initiate the therapeutic energy delivery cycle.

Foot control console (280) also includes hover sensor (284) associated with activation switch (282). Hover sensor (284) is in operative communication with control unit (250). During exemplary use, hover sensor (284) is configured to generate a hover zone (286), which is proximate to activation switch (282). Hover sensor (284) is configured to detect and/or identify an object within hover zone (286) and communicate that detection to control unit (250). In particular, hover zone (286) is suitably dimensioned to detect when a surgeon anticipates pressing activation switch (282) to initiate a therapeutic energy delivery cycle. Hover sensor (284) may include any suitable components as would be apparent to one skilled in the art in view of the teachings herein. As will be described in greater detail below, control unit (250) may initiate a sub-therapeutic energy cycle in response to hover sensor (284) detecting a surgeon's foot within hover zone (286). Such a sub-therapeutic energy cycle may determine suitable tissue characteristics, such that control unit (250) may suitably modify the energy delivery cycle in accordance with the description herein.

In one example, hover sensor (284) may be positioned above activation switch (282) to thereby project hover zone (286) to cover an area between activation switch (282) and hover sensor (284). In an alternative example, hover sensor (284) may be positioned next to or within a portion of activation switch (282) and include hover zone (286) capable of detecting an object immediately above and/or near activation switch (282). Hover sensor (284) may be positioned at any suitable location as would be apparent to one skilled in the art in view of the teachings herein. Hover zone (286) may include any suitable dimensions as would be apparent to one skilled in the art in view of the teachings herein.

Hover sensor (284) may be capable of detecting a nearby object through the use of a proximity, infrared, mechanical, laser detection component or any other component reasonably capable of detecting an object within hover zone (286). In one embodiment, an operator enters hover zone (286) prior to being capable of contacting activation switch (282). Control console (260), display unit (270), and/or foot control console (280) may be in either wired or wireless communication with control unit (250) and with each other.

C. Example of Surgical Instrument with Sub-Therapeutic Energy Delivery

Figure 6:
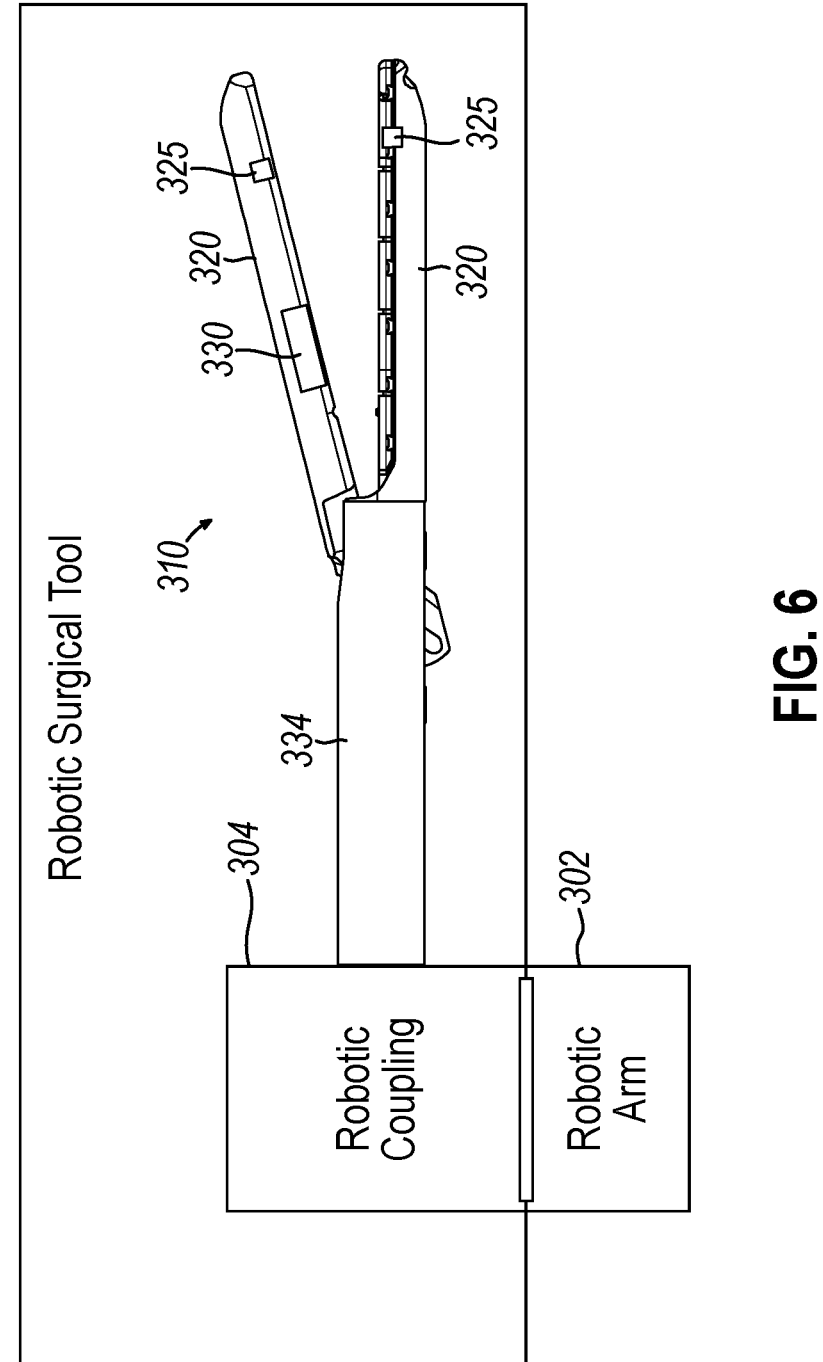
FIG. 6 depicts a schematic view of the robotic surgical tool of FIG. 2 that includes an end effector including a pair of jaws each having a respective electrode surface, and an Electrical Impedance Spectroscopy (EIS) sensor, the end effector being coupled to a robotic coupling via a shaft assembly, the robotic coupling being coupled to the robotic arm.

FIG. 6 shows an example of a surgical instrument (300) coupled to a robotic arm (302) via a robotic coupling (304). Surgical instrument (300), robotic coupling (304), and robotic arm (302) may be substantially similar to surgical instrument (114), tool driver adapter (124), and robotic arm (110) described above, with differences elaborated below. Therefore, robotic arm (302) and surgical instrument (300) may be readily incorporated into robotic surgical system (10) in replacement of robotic arm (110) and surgical instrument (114) described above, respectively.

In the current example, surgical instrument (300) includes an end effector (310) coupled to robotic coupling (304) via a shaft assembly (334). Shaft assembly (334) may be substantially similar to shaft assembly (134) described above, with differences elaborated herein. End effector (310) includes a pair of jaws (320) operable to grasp and to clamp tissue between each jaw (320). In particular, jaws (320) may be operatively coupled to robotic coupling (304) such that suitable rotary drives (not shown) of robotic arm (302) may drive jaws (320) between an open configuration (see FIGS. 6-7A) and various closed configurations (see FIGS. 7B-7C). Rotary drives (not shown) of robotic arm (302) may be substantially similar to rotary drives (136a, 136b, 136c, 136d, 136e, 136f) described above. Therefore, a surgeon may control the position of jaws (320) utilizing surgeon console (240) in accordance with the description herein.

In the current example, each jaw (320) includes an electrode (325). Electrodes (325) are configured to apply therapeutic energy in the form of RF energy to tissue grasped between jaws (320) in the closed configuration. In the current example, each jaw (320) includes a respective electrode (325) such that electrodes (325) are capable of conducting bipolar RF energy through tissue between jaws (320). In some examples, a single jaw (320) includes more than one electrode (325). Alternatively, or optionally, only one jaw (320) may include an electrode (325), or only one electrode (325) may be capable of applying RF energy tissue in a monopolar setup. Electrodes (325) may be suitably activated to deliver therapeutic energy in response to a surgeon pressing activation switch (282) in accordance with the description herein. While in the current example, end effector (310) includes a pair of jaws (320) and electrodes (325) configured to apply therapeutic energy to tissue, end effector (310) may include any other suitable means of delivering therapeutic energy to tissue as would be apparent to one skilled in the art in view of the teachings herein. For example, end effector (310) may include a clamp arm and an ultrasonic blade configured to apply therapeutic energy in the form of ultrasonic energy. As another example, end effector (310) may include a stapling assemblies configured to grasp tissue and apply therapeutic energy in the form of severing and stapling grasped tissue.

End effector (310) may also include a sub-therapeutic tissue sensor, such as an Electrical Impedance Spectroscopy (EIS) sensor (330) capable of sensing electrical impedance of tissue. EIS sensor (330) in communication with control unit (250) of surgeon console (240) such that sensor (330) is configured to transmit suitable data to control unit (250). As will be described in greater detail below, EIS sensor (330) may be activated by hover sensor (284) (see FIG. 5) detecting at least a portion of a surgeon's foot being present within hover zone (286). Once activated, EIS sensor (330) is configured to deliver sub-therapeutic energy to the grasped tissue, thereby acquiring impedance measurements on tissue and/or other suitable data as would be apparent to one skilled in the art in view of the teachings herein.

As mentioned above, EIS sensor (330) is configured to transmit impedance readings and/or data to control unit (250). Control unit (250) may utilize data from EIS sensor (330) to determine the type and/or density of tissue being grasped, the state of tissue being grasped, and/or other suitable characteristics of grasped tissue as would be apparent to one skilled in the art in view of the teachings herein. Further, in response to the determined characteristics of grasped tissue, control unit (250) may modify the process of delivering therapeutic energy to tissue to better accommodate the determined characteristics of tissue. For example, control unit (250) may modify the grasping force jaws (320) impart on tissue, the intensity of therapeutic energy to be delivered to tissue, the frequency and/or duration of thera-peutic energy to be delivered to tissue, and/or any other suitable modifications as would be apparent to one skilled in the art in view of the teachings herein. While in the current example, sub-therapeutic tissue sensor includes an EIS sen-sor (330), any other suitable sensor configured to provide suitable data regarding tissue may be utilized as would be apparent to one skilled in the art in view of the teachings herein.

EIS sensor (330) may be located at any suitable position on end effector (310) configured to acquire suitable data regarding tissue. EIS sensor (330) may be positioned along either jaw (320) or may be positioned proximal to jaw (320). EIS sensor (330) may be located in proximity to electrode (325) and also at an adequate distance such as to not be damaged when electrode (325) activates with RF energy. Alternatively, EIS sensor (330) may be incorporated into a portion of electrode (325) or around electrode (325) such that EIS sensor (330) is proximately located to tissue that is in contact with electrode (325). In examples where elec-trodes (325) are not used, EIS sensor (330) may be placed at a suitable location as to not interfere with the therapeutic energy being delivered to tissue.

Figure 7A:
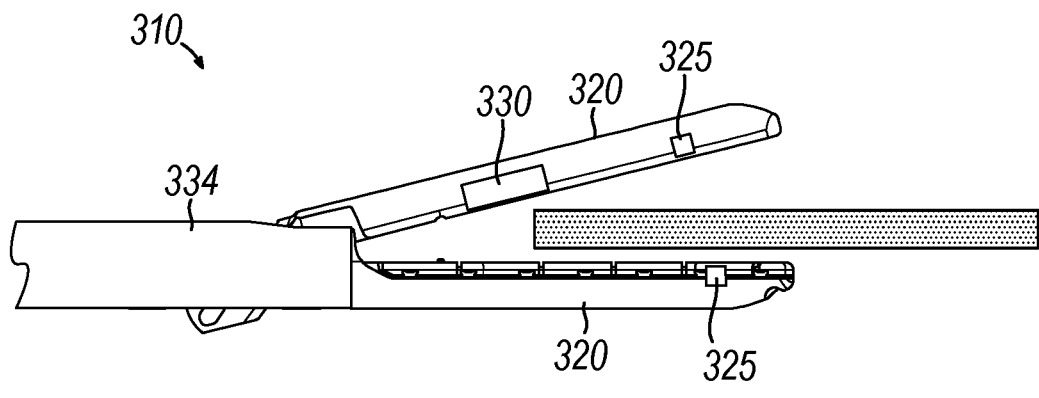
FIG. 7A depicts an elevational side view of the end effector of FIG. 6 with tissue between the pair of jaws in an open position.

D. Exemplary Use of Foot Control Console Having Hover Sensor and Surgical Instrument with Sub-Therapeutic Energy Delivery FIGS. 7A-8C show an exemplary use of robotic surgical system (10) having surgical instrument (300) and foot con-trol console (280) to acquire tissue characteristics via EIS sensor (330) and potentially modify the therapeutic energy delivered to accommodate for the measured tissue charac-teristics Once end effector (310) is suitably positioned within patient in accordance with the description herein, the sur-geon may utilize suitable portions of control console (260, 280) to initiate grasping (415) of tissue. As best shown in FIG. 7A, end effector (310) may be actuated such that jaws (320) are in the open configuration. With jaws (320) in the open configuration, end effector (310) may be positioned such that tissue is interposed between the pair of jaws (320). While in the open configuration, tissue may not be secured by end effector (310) so as to allow end effector (310) to engage differing portions of tissue. An operator may visually confirm, such as through an endoscope, that tissue intended for grasping is appropriately between pair of jaws (320) in the open configuration. At the moment shown in FIG. 7A, surgeon may not be ready to apply therapeutic energy to tissue in accordance with the description herein. Therefore, as best shown in FIG. 8A, the foot of the surgeon may not be adjacent to activation switch (282) nor within hover zone (286). With operator outside of hover zone (286), control unit (250) does not activate EIS sensor (330) in accordance with the description herein such that sub-therapeutic energy is not administered.

Figure 7B:
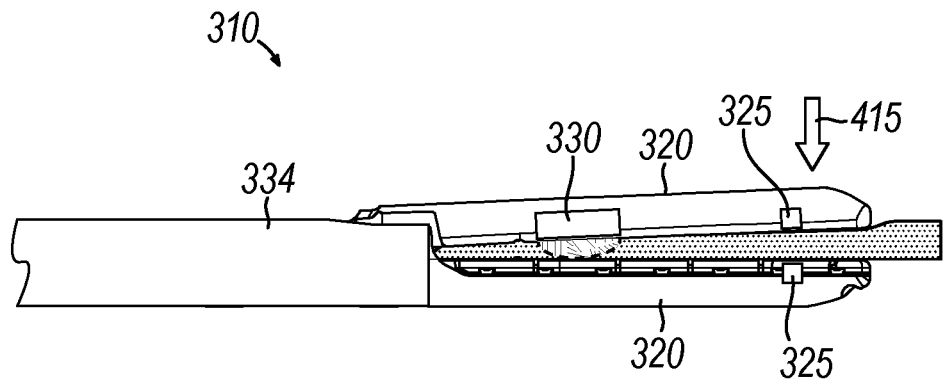
FIG. 7B depicts an elevational side view of the end effector of FIG. 6 with the pair of jaws initially grasping the tissue and the EIS sensor transmitting sub-therapeutic energy to the tissue.
Figure 8A:
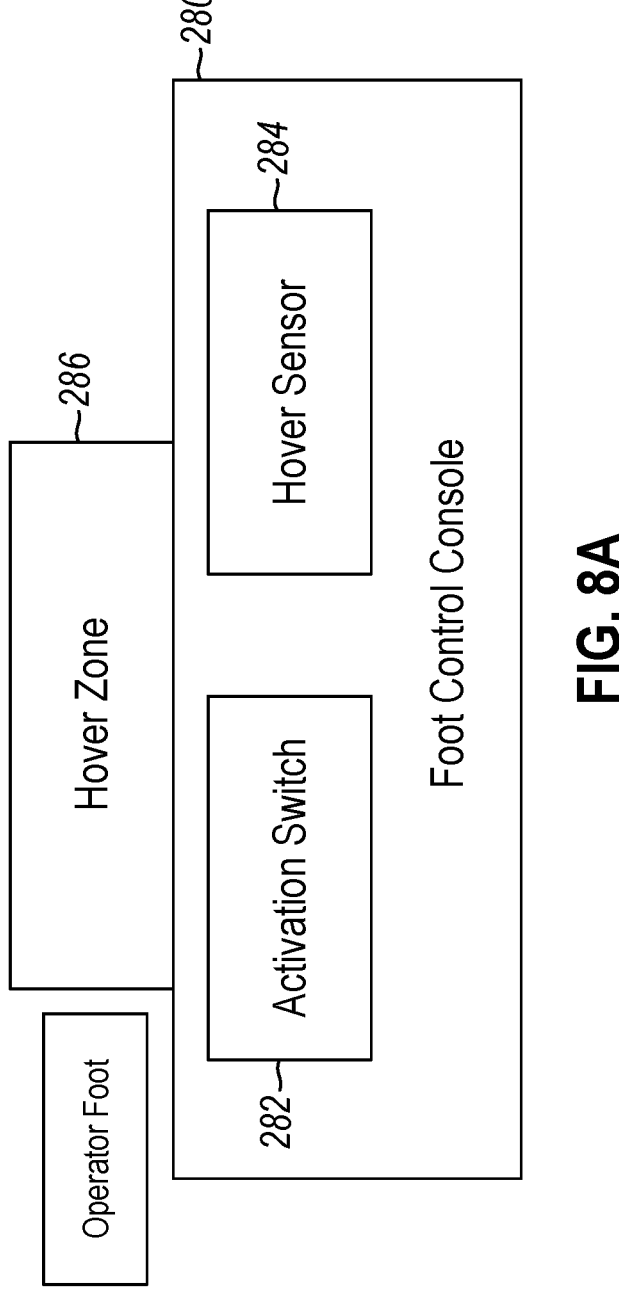
FIG. 8A depicts an elevational side view of the foot control console of FIG. 4 having an operator foot outside of the hover zone.

Next, as shown in FIG. 7B, end effector (310) is actuated from the open configuration toward a first closed configu-ration to thereby grasp tissue in preparation of applying therapeutic energy. While in the first closed configuration, jaws (320) are suitably engaged with tissue such that EIS sensor (330) is capable of transmitting sub-therapeutic energy to tissue and to thereby detect the electrical imped-ance of tissue. Electrodes (325) may also be in suitable contact with tissue and capable of delivering therapeutic energy to tissue in the form of RF energy.

Figure 8B:
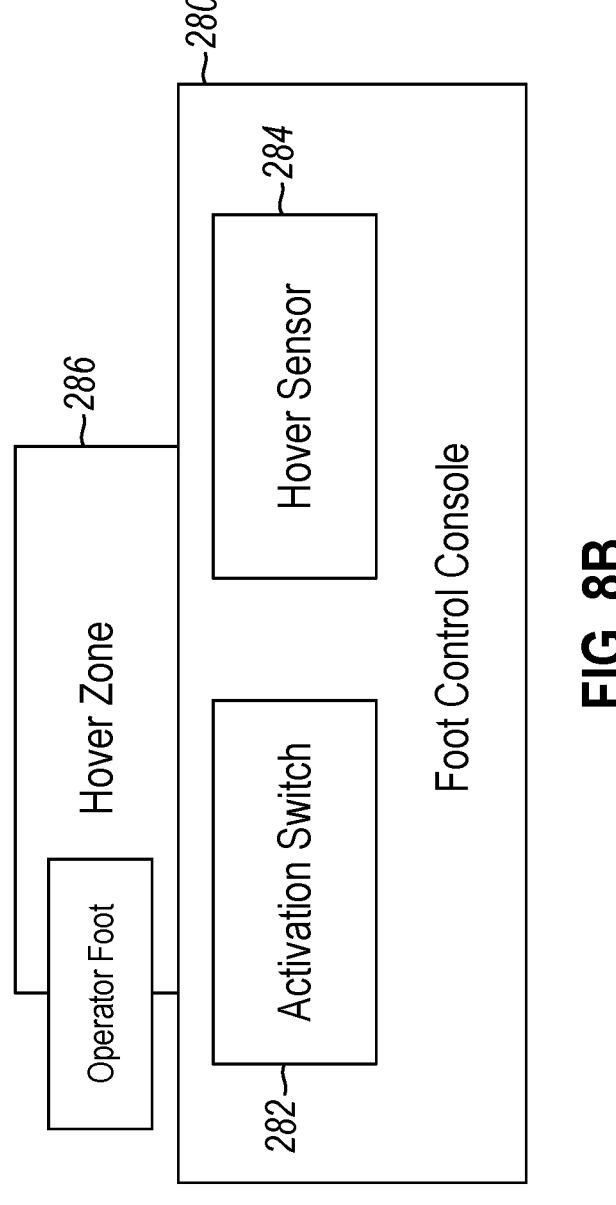
FIG. 8B depicts an elevational side view of the foot control console of FIG. 4 having the operator foot inside the hover zone and not pressing the activation switch of FIG. 5.

As shown in FIG. 8B, with jaws (320) grasping tissue in the first closed position, surgeon may hover their foot over activation switch (282) and within hover zone (286) in anticipation of pressing activation switch (282) to suitably activate electrodes (325) in accordance with the description herein. With foot detected within hover zone (286) by hover sensor (284), hover sensor (284) sends a confirmation signal to control unit (250) to enable EIS sensor (330) to deliver sub-therapeutic energy waves in the form of impedance sensing of tissue, as shown in FIG. 7B.

Control unit (250) may analyze the data provided by EIS sensor (330) in order to determine tissue characteristics. In some instances, tissue characteristics may be determined by EIS sensor (330) data falling within predetermined ranges, or thresholds. Further, control unit (250) may modify the clamping force provided by jaws (320) and/or the therapeu-tic energy to be delivered to tissue once activation switch (282) is suitably pressed. Intensity, duration, frequency, or any other suitable modifications of therapeutic energy may be made in response to the determined tissue characteristics. In some instances, control unit (250) may also determine the status of tissue and communicate that status to operator by report that status on display unit (270).

Figure 7C:
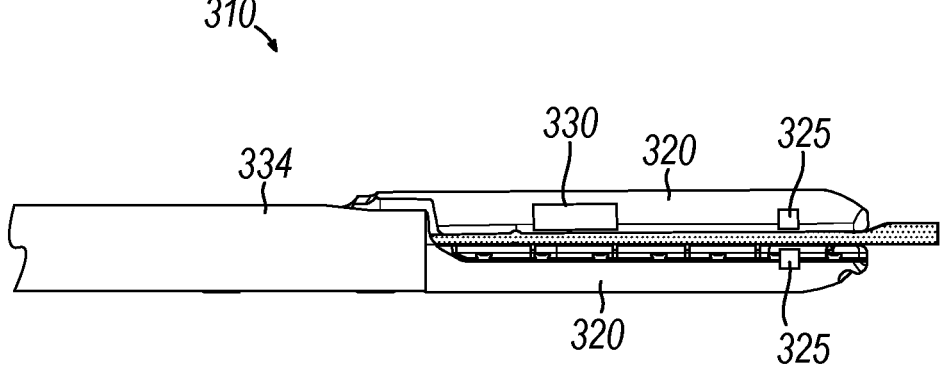
FIG. 7C depicts an elevational side view of the end effector of FIG. 6 with the pair of jaws further grasping the tissue and the electrode surfaces activated.

FIG. 7C shows end effector (310) modifying the clamping force of jaws (320) in response to tissue characteristics determined by control unit (250). It should be understood that such a modification of clamp force may be made before or after a surgeon presses activation switch (282) in accor-dance with the description herein. In the current example, end effector (310) moves jaws (320) into a second closed configuration. In the second closed configuration, jaws (320) impart a greater closure force onto tissue. Control unit (250) may transition end effector (310) from the first closed configuration to the second closed configuration based on readings from EIS sensor (330). While in the current example, jaws (320) are actuated closer together based on the readings from EIS sensor (330), in some examples, based on the determined tissue characters, jaws (320) may be actuated to slightly open based on the readings from EIS sensor (330) such that jaws (320) impart less clamping force onto tissue. Therefore, the closure force jaws (320) impart on tissue may be customizable based on the tissue charac-teristics determined by control unit (250) and sensor (330).

Figure 8C:
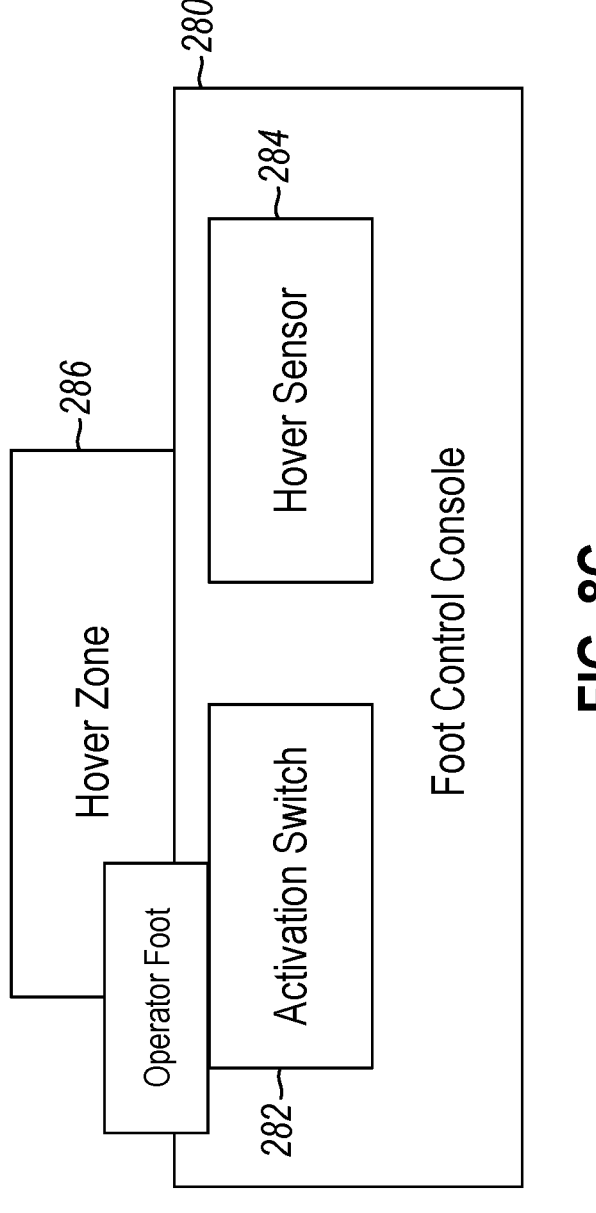
FIG. 8C depicts an elevational side view of the foot control console of FIG. 4 having the operator foot inside the hover zone and pressing the activation switch of FIG. 5.

As shown in FIG. 8C, once the surgeon is ready to administer therapeutic energy to tissue, surgeon may press activation switch (282). In response, control unit (250) may instruct jaws (320) to actuate into a desired closed configu-ration suitable to activate electrodes (325) for applying therapeutic energy to grasped tissue. Additionally, control unit (250) may instruct electrode (325) to apply such thera-peutic energy to grasped tissue.

It should be understood that since EIS sensor (330) is activated in response to hover sensor (284) detecting the presence of foot, sensor (330) and control unit (250) may obtain and utilize the above mentioned tissue characteristic data and make the above mentioned therapeutic energy modifications prior to the surgeon pressing activation switch (282). Therefore, in some instances, the tissue characteristic data and subsequent modifications may be made prior to a surgeon pressing activation switch (282); which may allow for customizable therapeutic energy delivery based on tissue characteristics without having to undesirable lengthen the amount of time between pressing activation switch (282) and completing a therapeutic energy delivery cycle.

In some instances, a surgeon may not wait for sensor (330) and control unit (250) to suitably acquire tissue information and make subsequent modifications in accor-dance with the description herein. For example, in some instances, a surgeon may press activation switch (282) without hovering over activation switch (282) long enough for sensor (330) and control unit (250) to make the above-mentioned determinations and modifications. In such instances, end effector (310) may be activated at a predetermined therapeutic energy delivery cycle and jaws (320) at a predetermined closed configuration. Therefore, if desirable, a surgeon may bypass the modification process initiated by hovering foot within hover zone (286).

Figure 9:
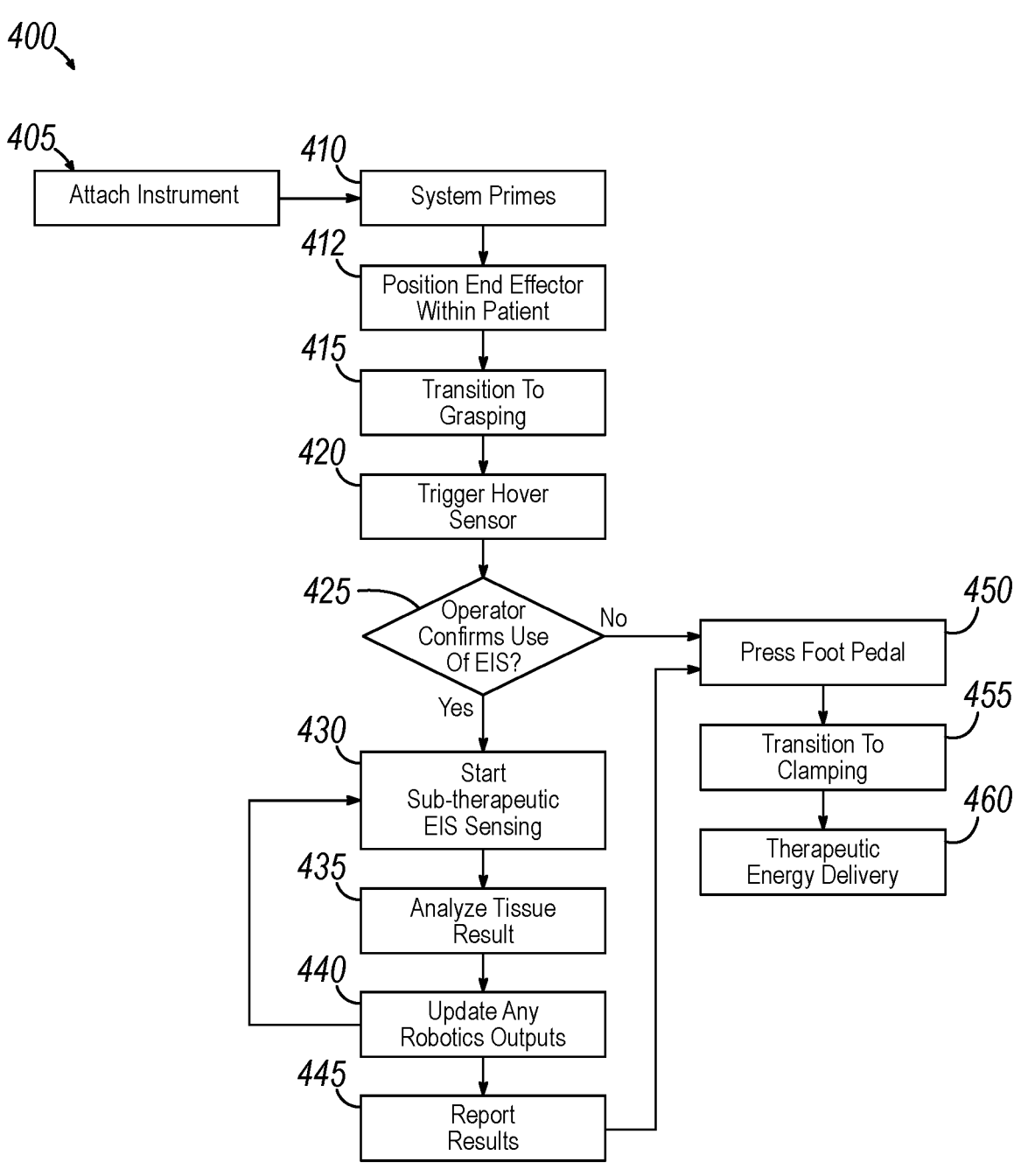
FIG. 9 depicts a flowchart of an illustrative use of the end effector of FIG. 6 and the surgeon console of FIG. 4 in conjunction with the robotic system of FIG. 1.

FIG. 9 shows a flow chart (400) demonstrating an exemplary use of robotic surgical system (10) having surgical instrument (300) and foot control console (280) to acquire tissue characteristics via EIS sensor (330) and potentially modify the therapeutic energy delivery to accommodate for the measured tissue characteristics. First, surgical instrument (300) may be operatively attached (405) to robotic arm (302) in accordance with the description herein. Surgical instrument (300) may be attached (405) to robotic arm (302) via robotic coupling (304) such that suitable components of end effector (310) are in communication with control unit (250).

Once in communication, robotic surgical system (10) may prime (410) itself with a series of checks and operations to ensure operational readiness. For example, robotic surgical system (10) may identify the type of surgical instrument (300) attached (405) to robotic arm (302). Once suitably identified, priming (410) may include loading suitable operational parameters to ensure control unit (250) suitably controls end effector (310) in accordance with the description herein. Additionally, priming (410) may include ensuring electrical continuity between control unit (250) and various electrically controlled components of end effector (310), such as electrode (325) and EIS sensor (330). Priming surgical instrument (300) for suitable use with robotic surgical system (10) may include any other suitable processes as would be apparent to one skilled in the art in view of the teachings herein.

Next, once surgical system (10) is primed (410) and ready for exemplary use, surgical instrument (300) is inserted into the patient via a cannula (not shown), which may be substantially similar to cannula (120) described above. The distal end of surgical instrument (300), including end effector (310), is suitably positioned (412) within patient such that end effector (310) is adjacent to targeted anatomical structure. Positioning (412) of end effector (310) may be controlled using surgeon console (240) in accordance with the description herein. Therefore, surgeon may visually confirm suitable placement of end effector using display unit (270).

Next, surgeon may control end effector (310) in accordance with the description herein to suitably grasp (415) tissue. With tissue grasped (415), surgeon may be ready to apply therapeutic energy to tissue, such that surgeon hovers their foot over activation switch (282), thereby triggering (420) hover sensor (284). As mentioned above, a surgeon may choose to utilize the sub-therapeutic energy process, or choose to press activation switch prior to the completion of the sub-therapeutic energy process. Therefore, surgeon may confirm use (425) of sensor (230) by keeping their foot within the hover zone (288) or choose to bypass the use of sensor (230) by pressing (450) activation switch (282) prior to completion of the sub-therapeutic energy process.

If the surgeon confirms use (425) of sub-therapeutic energy process, control unit (250) may start (430) the sub-therapeutic process and instruct activation of EIS sensor (330) in accordance with the description herein. Next, control unit (250) may analyze (435) the tissue results provided by sensor (430) and update (440) the robotic outputs (such as modifying therapeutic energy deliver or clamp force) in response to such an analysis (435). Optionally, control unit (250) may report result (445) via display unit (270).

Next, the surgeon may press (450) activation switch (232) to deliver therapeutic energy (460) in accordance with the description herein. In instances where clamping force provided by jaws (320) is changed after activation switch (232) is pressed, jaws (320) may then transition (455) into the determined closed position. It should be understood that if the surgeon bypasses the sub-therapeutic sensing process, pressing (450) activation switch (232) will activate a predetermined therapeutic energy delivery (460) (i.e. a therapeutic energy delivery cycle that is not based on tissue characteristics results provided by sensors (330) and control unit (250)). However, if surgeon does not bypass the sub-therapeutic sensing process, pressing (450) activation switch (232) activates a customized therapeutic energy delivery (460) that utilizes tissue characteristics results provided by sensor (330) and control unit (250). In some instances, a surgeon may complete the sub-therapeutic energy process in accordance with the description herein, and still decide to ignore the results and activate a therapeutic energy cycle that is not based on the determined tissue characteristics.

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A robotic surgical system, comprising: a robotic arm including a distal end; a tool driver operatively coupled with the distal end of the robotic arm; a control unit; a surgical instrument comprising: an end effector configured to transmit therapeutic energy to tissue via a therapeutic energy cycle based on instructions from the control unit; and an tissue sensor configured to determine at least one tissue characteristic and transmit the at least one tissue characteristic to the control unit, wherein the control unit is configured to modify the therapeutic energy cycle based on the at least one tissue characteristic; and a control console including: an activation switch configured to activate the therapeutic energy cycle of the end effector, and a hover sensor configured to sense an object proximate to the activation switch within a hover zone, wherein the hover sensor is configured to activate the tissue sensor to determine the at least one tissue characteristic in response to sensing the object within the hover zone.

Example 2

The robotic surgical system of any one or more the preceding Examples, wherein the tissue sensor comprises an electrical impedance sensing device configured to determine an electrical impedance of the tissue.

Example 3

The robotic surgical system of any one or more the preceding Examples, wherein the control console comprises a foot control console, wherein the hover sensor is configured to sense a foot of an operator.

Example 4

The robotic surgical system of any one or more the preceding Examples, wherein the hover zone is positioned at least above the activation switch, the foot control console being configured for the operator to enter the hover zone before activation switch can activate the therapeutic energy cycle of the end effector.

Example 5

The robotic surgical system of any one or more the preceding Examples, wherein the end effector comprises an electrode configured to deliver RF energy.

Example 6

The robotic surgical system of any one or more the preceding Examples, wherein the end effector comprises a pair of jaws configured to grasp tissue, wherein the control unit is configured to modify a grasping force of the pair of jaws based on the at least one tissue characteristic.

Example 7

The robotic surgical system of any one or more the preceding Examples, wherein at least one jaw of the pair of jaws includes an electrode.

Example 8

The robotic surgical system of any one or more the preceding Examples, wherein the electrode is configured to ablate tissue.

Example 9

The robotic surgical system of any one or more the preceding Examples, wherein the surgical instrument comprises a robotic interface configured to selectively couple with the tool driver.

Example 10

The robotic surgical system of any one or more the preceding Examples, wherein the surgical instrument comprises a shaft assembly extending proximally from the end effector.

Example 11

The robotic surgical system of any one or more the preceding Examples, further comprising a display unit, wherein the display unit is configured to communicate the at least one tissue characteristic determined by the tissue sensor.

Example 12

The robotic surgical system of any one or more the preceding Examples, wherein the surgical instrument is removably coupled to the robotic arm.

Example 13

The robotic surgical system of any one or more the preceding Examples, wherein the control unit is configured to modify an intensity of an therapeutic energy cycle based on the at least one tissue characteristic.

Example 14

The robotic surgical system of any one or more the preceding Examples, wherein the control unit is configured to modify a duration of the therapeutic energy cycle based on the at least one tissue characteristic.

Example 15

The robotic surgical system of any one or more the preceding Examples, wherein the control unit is configured to modify a frequency of the therapeutic energy cycle based on the at least one tissue characteristic.

Example 16

The robotic surgical system of any one or more the preceding Examples, wherein the control unit is associated with the control console.

Example 17

A surgeon console, comprising: a control unit; a control console configured to receive commands from an operator and communicate the commands to the control unit; a robotic arm in communication with the control unit; a surgical instrument configured to selectively couple with the robotic arm, the surgical instrument comprising an end effector configured to deliver therapeutic energy to tissue, the end effector comprising: a pair of jaws configured to grasp tissue with an adjustable compression, and a tissue sensor configured to determine at least one tissue characteristic and transmit the at least one tissue characteristic to the control unit, wherein the control unit is configured to modify the adjustable compression of the pair of jaws in response to the at least one tissue characteristic; and a foot control console in communication with the control console and including: an activation switch configured to activate the end effector with therapeutic energy, and a hover sensor configured to sense an object proximate to the activation switch within a hover zone, wherein the hover sensor is configured to activate the tissue sensor to determine the at least one tissue characteristic in response to sensing the object within the hover zone.

Example 18

A method of activating an end effector, comprising: receiving indication from a hover sensor that an object has entered a hover zone defined by the hover sensor and positioned proximate to an activation switch; in response to receiving indication from the hover sensor, instructing a tissue sensor to determine at least one tissue characteristic of tissue adjacent to the tissue sensor; utilizing the at least one tissue characteristic to modify a first therapeutic energy to a second therapeutic energy to be delivered to tissue; and receiving indication that activation switch has been pressed; and activating the end effector with the second therapeutic energy as modified based on the at least one tissue characteristic.

Example 19

The method of Example 18, wherein the at least one tissue characteristic comprises an electrical impedance.

Example 20

The method of Example 18, wherein the hover zone is positioned at least above the activation switch.

IV. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of uterine manipulator instruments, it should be understood that various teachings herein may be readily applied to a variety of other types of devices. By way of example only, the various teachings herein may be readily applied to other types of surgical instruments including tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A robotic surgical system, comprising:
   (a) a robotic arm including a distal end;
   (b) a tool driver operatively coupled with the distal end of the robotic arm;
   (c) a control unit;
   (d) a surgical instrument comprising:
       (i) an end effector configured to transmit therapeutic energy to tissue via a therapeutic energy cycle based on instructions from the control unit; and
       (ii) an tissue sensor configured to determine at least one tissue characteristic and transmit the at least one tissue characteristic to the control unit, wherein the control unit is configured to modify the therapeutic energy cycle based on the at least one tissue characteristic; and
   (e) a control console including:
       (i) an activation switch configured to activate the therapeutic energy cycle of the end effector, and
       (ii) a hover sensor configured to sense an object proximate to the activation switch within a hover zone, wherein the hover sensor is configured to activate the tissue sensor to determine the at least one tissue characteristic in response to sensing the object within the hover zone.

2. The robotic surgical system of claim 1, wherein the tissue sensor comprises an electrical impedance sensing device configured to determine an electrical impedance of the tissue.

3. The robotic surgical system of claim 1, wherein the control console comprises a foot control console, wherein the hover sensor is configured to sense a foot of an operator.

4. The robotic surgical system of claim 3, wherein the hover zone is positioned at least above the activation switch, the foot control console being configured for the operator to enter the hover zone before activation switch can activate the therapeutic energy cycle of the end effector.

5. The robotic surgical system of claim 1, wherein the end effector comprises an electrode configured to deliver RF energy.

6. The robotic surgical system of claim 1, wherein the end effector comprises a pair of jaws configured to grasp tissue, wherein the control unit is configured to modify a grasping force of the pair of jaws based on the at least one tissue characteristic.

7. The robotic surgical system of claim 6, wherein at least one jaw of the pair of jaws includes an electrode.

8. The robotic surgical system of claim 7, wherein the electrode is configured to ablate tissue.

9. The robotic surgical system of claim 1, wherein the surgical instrument comprises a robotic interface configured to selectively couple with the tool driver.

10. The robotic surgical system of claim 9, wherein the surgical instrument comprises a shaft assembly extending proximally from the end effector.

11. The robotic surgical system of claim 1, further comprising a display unit, wherein the display unit is configured to communicate the at least one tissue characteristic determined by the tissue sensor.

12. The robotic surgical system of claim 1, wherein the surgical instrument is removably coupled to the robotic arm.

13. The robotic surgical system of claim 1, wherein the control unit is configured to modify an intensity of a therapeutic energy cycle based on the at least one tissue characteristic.

14. The robotic surgical system of claim 1, wherein the control unit is configured to modify a duration of the therapeutic energy cycle based on the at least one tissue characteristic.

15. The robotic surgical system of claim 1, wherein the control unit is configured to modify a frequency of the therapeutic energy cycle based on the at least one tissue characteristic.

16. The robotic surgical system of claim 1, wherein the control unit is associated with the control console.

17. A surgeon console, comprising:
   (a) a control unit;
   (b) a control console configured to receive commands from an operator and communicate the commands to the control unit;
   (c) a robotic arm in communication with the control unit;
   (d) a surgical instrument configured to selectively couple with the robotic arm, the surgical instrument comprising an end effector configured to deliver therapeutic energy to tissue, the end effector comprising:
       (i) a pair of jaws configured to grasp tissue with an adjustable compression, and
       (ii) a tissue sensor configured to determine at least one tissue characteristic and transmit the at least one tissue characteristic to the control unit, wherein the control unit is configured to modify the adjustable compression of the pair of jaws in response to the at least one tissue characteristic; and
   (d) a foot control console in communication with the control console and including:
       (i) an activation switch configured to activate the end effector with therapeutic energy, and
       (ii) a hover sensor configured to sense an object proximate to the activation switch within a hover zone, wherein the hover sensor is configured to activate the tissue sensor to determine the at least one tissue characteristic in response to sensing the object within the hover zone.

18. A method of activating an end effector, comprising:
   (i) receiving indication from a hover sensor that an object has entered a hover zone defined by the hover sensor and positioned proximate to an activation switch;
   (ii) in response to receiving indication from the hover sensor, instructing a tissue sensor to determine at least one tissue characteristic of tissue adjacent to the tissue sensor;
   (iii) utilizing the at least one tissue characteristic to modify a first therapeutic energy to a second therapeutic energy to be delivered to tissue; and
   (iv) receiving indication that activation switch has been pressed; and
   (v) activating the end effector with the second therapeutic energy as modified based on at least one tissue characteristic.

19. The method of claim 18, wherein the at least one tissue characteristic comprises an electrical impedance.

20. The method of claim 18, wherein the hover zone is positioned at least above the activation switch.

\* \* \* \* \*